(12) United States Patent
Lizcano

(10) Patent No.: US 6,352,979 B1
(45) Date of Patent: Mar. 5, 2002

(54) METHOD OF TREATING SNAKEBITE AND COMPLICATIONS RESULTING THEREFROM

(76) Inventor: Lucinda Lizcano, 743 W. Theo Ave., San Antonio, TX (US) 78225

( * ) Notice: Subject to any disclaimer, the term of this patent is extended or adjusted under 35 U.S.C. 154(b) by 0 days.

(21) Appl. No.: 09/933,238

(22) Filed: Aug. 20, 2001

(51) Int. Cl.$^7$ ..................... A61K 31/66; A61K 31/185
(52) U.S. Cl. ........................................ 514/127; 514/578
(58) Field of Search .................................. 514/127, 578

(56) References Cited

U.S. PATENT DOCUMENTS

| | | | | |
|---|---|---|---|---|
| 4,220,660 A | * | 9/1980 | Brock | 424/315 |
| 5,789,000 A | * | 8/1998 | Hausheer et al. | 424/649 |
| 6,177,411 B1 | * | 1/2001 | Hausheer | 514/108 |

* cited by examiner

*Primary Examiner*—Raymond Henley, III
(74) *Attorney, Agent, or Firm*—Thomas J. Dodd

(57) ABSTRACT

This invention relates to a method of treating snakebite victims, especially those at risk from neurotoxic effects from snakebite or those already exhibiting symptoms of neurotoxicity. The method includes administering to a patient in need of treatment an effective amount of a thiol or reducible disulfide compound according to the formula set forth in the specification.

4 Claims, No Drawings

METHOD OF TREATING SNAKEBITE AND COMPLICATIONS RESULTING THEREFROM

FIELD OF THE INVENTION

This invention relates to a method for treating a patient suffering from snakebite, or from complications caused thereby, particularly the neurotoxicity associated with bites from poisonous snakes. The method involves administering an effective amount of a disulfide or thiol-containing compound to a patient suffering from snakebite or from complications of snakebite.

BACKGROUND OF THE INVENTION

Each year, bites by poisonous snakes account for approximately 50,000 deaths worldwide. While most deaths occur in underdeveloped areas with little or no access to treatment, snakebite remains a serious health concern. In the United States, more than 45,000 cases of snakebite are reported every year, approximately 8,000 of which are bites from poisonous snakes.

On average, 15 to 25 people die from snakebite in the United States, and hundreds of others suffer from snakebite effects. These effects can be mild and reversible, or moderate to severe, and depend upon several factors: length of time since the bite, sensitivity of the victim to the snake's venom, amount of venom injected, distribution of the venom beyond the bite site, initial first aid rendered, and others.

Another potential problem in the treatment of poisonous snakebite is the hypersensitivity of many victims to the antivenin serum. Conventional antivenin is derived from the serum of immune horses, and can provoke serious hypersensitivity reactions when administered to snakebite victims.

Snake venom is comprised of several compounds, including complex polypeptides, enzymes, glycoproteins, and numerous small molecular weight compounds, both organic and inorganic. Toxicities from snakebite are often multi-systemic, as well as local, and depend on a number of factors, both snake and human.

Systemic snakebite toxicities include among others, potentially severe and irreversible neurotoxicity. Victims often experience severe pain in the area of the bite and elsewhere where the venom has spread. Victims also have exhibited paresthesia, numbness, paralysis, as well as tics, twitching and other involuntary reflexive actions. Though not often life threatening, neurotoxicity adversely affects quality of life of the victim.

Mesna (sodium 2-mercaptoethene sulfonate) and dimesna (disodium 2,2'-dithiobis ethane sulfonate) are known therapeutic compounds that have heretofore demonstrated a wide variety of therapeutic uses. Both mesna and dimesna have been shown to be effective protective agents against certain specific types of toxicity associated with the administration of cytotoxic drugs used to treat patients for various types of cancer.

In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

The near absence of toxicity of dimesna further underscores the usefulness of this compound, as large doses can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The molecular structures of both mesna and dimesna are shown below as Structure I and Structure II respectively.

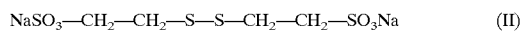

As shown, dimesna is a dimer of mesna, with the optimum conditions for oxidation occurring in the slightly basic (pH~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with certain platinum agents and/or taxanes.

Dimesna, as well as some analogues, have excellent toxicity profiles in mammalian species. In fact, dimesna has been administered intravenously to mice and dogs in doses higher than the accepted oral $LD_{50}$ for common table salt (3750 mg/kg), with no adverse effects. Dimesna has also been administered to humans in doses exceeding 40 g/m$^2$, with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration, usually a hydroxy, aquo or superoxide is located. Mesna also tends to form conjugates with naturally occurring biochemicals that contain a free thiol moiety, such as cysteine, glutathione, homocysteine, and others.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well known in the art. One such method involves the two-step, single pot synthetic process for making dimesna and like compounds of the following formula:

$R_1$—S—$R_2$;

wherein:

$R_1$ is hydrogen, X-lower alkyl, or X-lower alkyl-$R_3$;

$R_2$ is -lower alkyl-$R_4$;

$R_3$ and $R_4$ are each individually $SO_3M$ or $PO_3M_2$;

X is absent or X is sulfur; and

M is an alkali metal.

The process essentially involves a two-step single pot synthetic process, which results in the conversion of an alkenyl sulfonate salt or acid to the desired formula I compound. The process in the case of mesna is a single step process that converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well known and documented in the prior art, may be employed to make either mesna or dimesna, or derivatives and analogues thereof.

SUMMARY OF THE INVENTION

This invention involves the administration of an effective amount of a compound of formula I, below, for treatment of snakebite complications, particularly the neurotoxicity associated with snakebite.

$$R_1\text{—S—}(\text{alkyl})_m\text{—}\overset{R_3}{\underset{}{|}}\text{—}R_2 \qquad (I)$$

wherein:

$R_1$ is hydrogen, lower alkyl or $$\text{—S—}(\text{alkyl})_m\text{—}\overset{R_5}{\underset{}{|}}\text{—}R_4;$$

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

Each m is individually 1, 2, 3, 4, 5 or 6 with the proviso that if m is 1, then $R_3$ is hydrogen; and M is hydrogen or an alkali metal ion; or a pharmaceutically acceptable salt thereof.

Effective amounts of the formula I compound to be administered according to the method of this invention are variable, and depend on the severity of the patient's condition.

Accordingly, it is an object of this invention to provide for a method of safely and effectively treating a snakebite victim.

Another object is to provide a method of treating a snakebite victim by administration of a thiol or reducible disulfide to the patient in need of treatment.

Other objects will become apparent upon a reading of the following description.

DESCRIPTION OF THE PREFERRED EMBODIMENT

The preferred embodiment herein described is not intended to be exhaustive or to limit the invention to the precise form disclosed. It is chosen and described to explain the principles of the invention, and its application and practical use to best enable others skilled in the art to follow its teachings.

The method of this invention involves the administration of an effective amount of a formula I compound to a snakebite victim. Administration may be either oral or parenteral.

The formula I compounds are postulated to alleviate the neurotoxicity associated with snakebite by binding to tubulin, therefore preventing or reducing the neurotoxic effects of snake venom on nerve fibers. The formula I compounds form conjugates with certain thiol-containing biochemicals, which serves to lower their toxicity profiles and provide for rapid elimination through the kidneys.

The effective amount of the formula I compound will necessarily depend upon the severity of the victim's condition. Assessed risk can be determined through the patient's medical history accompanied by standard tests to determine the extent and severity of envenomation. The higher the levels of venom in the victim's bloodstream, the higher the dose of the formula I compound to be administered.

Since the formula I compounds are essentially nontoxic, large amounts can be safely administered. The preferred dosage to treat neurotoxicity associated with snakebite may be as low as 0.1 mg/kg up to 3,000 mg/kg. The more severe the envenomation, the more formula I compound should be administered to provide an effective response.

Administration is preferably through parenteral or oral routes. For parenteral administration, the formula I compound is dissolved in a suitable solvent, most preferably water, to produce a solution that may be injected or infused. One or more pharmaceutically acceptable excipients may also be added to provide for an elegant formulation. Parenteral usage is favored for acute or especially severe neurotoxicity associated with snakebite.

For oral administration the formula I compound is preferably combined with one or more pharmaceutically acceptable excipients, fillers and/or diluents. Oral dosage forms may include pills, caplets, tablets, and others. Alternatively, the formula I compound may be contained in a deglutable container such as a gelatin capsule or the like.

The formula I compounds may be co-administered with conventional antivenin serum without affecting the potency of either agent.

Administration of the formula I compound should be made as soon as possible following diagnosis of neurotoxicity due to snakebite envenomation, preferably even before the onset of symptoms. Preferred initial dose is between 10 mg/kg and 1000 mg/kg. High doses may be repeated ad libitum. Careful observation and analysis is performed regularly after diagnosis as per accepted medical procedures for treating snakebite victims.

Other accepted methods of treatment may also be combined with the administration of the formula I compound. Due to the excellent safety profile, additional doses of the formula I compound may be administered safely if the initial dose does not produce an adequate response.

It is understood that the above description is in no way limiting of the invention, which may be modified within the scope of the following claims.

What is claimed is:

1. A method of treating a snakebite victim at risk of or exhibiting neurotoxicity, said method comprising administering to the victim an effective amount of a compound of formula I:

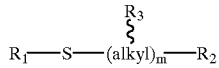
(I)

wherein:

$R_1$ is hydrogen, lower alkyl or

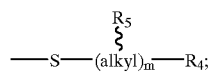

$R_2$ and $R_4$ are each individually $SO_3^- M^+$, $PO_3^{2-} M_2^{2+}$, or $PO_2S^{2-} M_2^{2+}$;

$R_3$ and $R_5$ are each individually hydrogen, hydroxy or sulfhydryl;

Each m is individually 1, 2, 3, 4, 5 or 6 with the proviso that if m is 1, then $R_3$ is hydrogen; and M is hydrogen or an alkali metal ion; or a pharmaceutically acceptable salt thereof.

2. The method of claim 1 wherein the effective amount of the formula I compound administered is from 0.1 mg/kg of body weight to 3,000 mg/kg of body weight.

3. The method of claim 1 wherein the compound is administered orally.

4. The method of claim 1 wherein the compound is administered parenterally.

* * * * *